(12) United States Patent
Chen et al.

(10) Patent No.: US 11,213,679 B2
(45) Date of Patent: Jan. 4, 2022

(54) PORTABLE ELECTRONIC DEVICE WITH TENS FUNCTION

(71) Applicant: MASSACHUSETTS NEURO TECHNOLOGY, INC., Weston, MA (US)

(72) Inventors: Cheng Chen, Weston, MA (US); Quan Xiao, Weston, MA (US); Yun Jiang, Weston, MA (US)

(73) Assignee: MASSACHUSETTS NEURO TECHNOLOGY, INC., Weston, MA (US)

( * ) Notice: Subject to any disclaimer, the term of this patent is extended or adjusted under 35 U.S.C. 154(b) by 109 days.

(21) Appl. No.: 16/135,442

(22) Filed: Sep. 19, 2018

(65) Prior Publication Data

US 2019/0105494 A1    Apr. 11, 2019

Related U.S. Application Data

(60) Provisional application No. 62/571,032, filed on Oct. 11, 2017.

(51) Int. Cl.
*A61N 1/36*    (2006.01)
*A61N 1/04*    (2006.01)

(52) U.S. Cl.
CPC ......... *A61N 1/3603* (2017.08); *A61N 1/0456* (2013.01); *A61N 1/36021* (2013.01)

(58) Field of Classification Search
CPC . A61N 1/18; A61N 1/20; A61N 1/205; A61N 1/26; A61N 1/32; A61N 1/322; A61N 1/326; A61N 1/328; A61N 1/36; A61N 1/36003; A61N 1/36014; A61N 1/36021; A61N 1/36025; A61N 1/3603; A61N 1/36125; A61N 1/36128; A61N 1/36146; A61N 1/36157; A61N 1/36164; A61N 1/00; A61N 1/02; A61N 1/025; A61N 1/0452; A61N 1/0456; A61N 1/0464; A61N 1/0468
USPC .............................. 607/2, 3, 45, 46, 48, 50
See application file for complete search history.

(56) References Cited

U.S. PATENT DOCUMENTS

| | | | |
|---|---|---|---|
| 9,764,133 B2* | 9/2017 | Thomas | A61N 1/36034 |
| 10,252,053 B2* | 4/2019 | Page | A61N 1/0456 |
| 2013/0253613 A1* | 9/2013 | Salahovic | A61N 1/205 607/61 |
| 2014/0194946 A1* | 7/2014 | Thomas | A61N 1/36034 607/46 |
| 2017/0368344 A1* | 12/2017 | Ironi | A61N 1/36021 |

* cited by examiner

*Primary Examiner* — Ahmed M Farah
(74) *Attorney, Agent, or Firm* — Anova Law Group, PLLC

(57) ABSTRACT

A portable electronic device includes a battery, a transcutaneous electrical nerve stimulation (TENS) circuit, a power management circuit, a first output unit, and a second output unit. The TENS circuit provides a TENS electrical current. The power management circuit is coupled to the battery and the TENS circuit for managing a power distribution of the portable electronic device. The first output unit receives the TENS electrical current from the TENS circuit and outputs the TENS electrical current to a user. The second output unit receives a power signal from the battery and outputs the power signal to an external electronic device.

17 Claims, 3 Drawing Sheets

PORTABLE ELECTRONIC DEVICE WITH TENS FUNCTION

FIELD OF THE DISCLOSURE

The present disclosure relates to a portable electronic device and, more particularly, relates to a portable electronic device with built-in transcutaneous electrical nerve stimulation (TENS) function.

BACKGROUND

Transcutaneous electrical nerve stimulation (TENS) is the use of electric pulse produced by a device to stimulate the different locations of body for therapeutic purposes. TENS covers the complete range of transcutaneously applied currents used for nerve excitation, and sometimes TENS is used with a more restrictive intent, namely to describe the kind of pulses produced by the stimulators used to treat pain.

TENS is widely used to treat disorders such as chronic pain and depression. TENS is usually connected to superficial electrodes, which provide stimulation to treat disorders. TENS machine works by sending stimulating pulses across the surface of the skin and along the nerve strands. Sometimes, by using different frequency, TENS can also produce similar effect as massage. When attached to needle, TENS can be used to apply electroacupuncture stimulation.

However, in the present market, TENS machine has only the stimulation function. TENS machine does not provide functions other than an electroacupuncture device or an electrical massage device. In addition, the user has to carry the conventional TENS machine and other electronic, devices such as the power bank or the cell phone, separately, and the size and the weight of multiple devices bring the user inconvenience. Hence, it is greatly desired to integrate the function of TENS with other portable electronic devices to extend the efficiency and convenience of the consuming electronics.

BRIEF SUMMARY OF THE DISCLOSURE

One aspect of the present disclosure provides a portable electronic device comprising a battery, a transcutaneous electrical nerve stimulation (TENS) circuit, a power management circuit, a first output unit and a second output unit. The TENS circuit provides a TENS electrical current. The power management circuit is coupled to the battery and the TENS circuit for managing a power distribution of the portable electronic device. The first output unit receives the TENS electrical current from the TENS circuit and outputs the TENS electrical current to a user. The second output unit outputs a second signal to an external electronic device. The second signal may be a power signal, an image displaying signal, a signal for driving a lamp, and so on.

Another aspect of the present disclosure provides a portable electronic device comprising a battery, a transcutaneous electrical nerve stimulation (TENS) circuit, a cellphone circuit, a power management circuit, a first output unit and a second output unit. The TENS circuit provides a TENS electrical current. The cellphone circuit provides at least a communication function and an audio outputting function. The power management circuit is coupled to the TENS circuit, the cellphone circuit and the battery for managing a power distribution between the TENS circuit and the cellphone circuit. The first output unit receives the TENS electrical current from the TENS circuit and outputs the TENS electrical current to a user. The second output unit receives an audio signal from the cellphone circuit and outputs the audio signal to the user.

A further aspect of the present disclosure provides a method for providing a transcutaneous electrical nerve stimulation (TENS) function in a portable electronic device. The method includes providing a power management circuit, a TENS circuit and a battery; managing a power distribution from the battery to the power management circuit and the TENS circuit; generating a TENS electrical current by the TENS circuit and providing the TENS electrical current to a user through a first output unit; and generating a power signal and providing the power signal to an external device through a second output unit.

Other aspects of the present disclosure can be understood by those skilled in the art in light of the description, the claims and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the invention, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present disclosure. Based on the disclosed embodiment, persons of ordinary skill in the art may derive other embodiments consistent with the present disclosure, all of which are within the scope of the embodiments of the present disclosure.

A transcutaneous electrical nerve stimulation (TENS) unit is a device that sends small electrical currents/pulses to targeted body parts. These currents are used to relieve pain or other symptoms. Some TENS units are designed for use in a hospital or healthcare facility. Others are safe to use at home. Most TENS units and portable electrotherapy devices operate on batteries. Usually, the higher the amplitude and frequency settings used, the shorter a battery will last. Most batteries are made up of individual cells that each hold a charge. The power of a battery is determined by how many cells there are inside a battery and how much charge they hold. Further, most TENS units are stand-alone units which require a user to carry it around.

Embodiments of the present disclosure integrate TENS functions into a portable electronic device, including a portable charger, power bank, cell phone, MP3 player, PDA, iPad, tablet, remote, laptop, desktop, radio, table lamp, and monitor. Embodiments of the present disclosure can significantly extent the function of the portable electronic device and provides a convenient way to the consumers for medical treatment or staying healthy.

Figure 1:
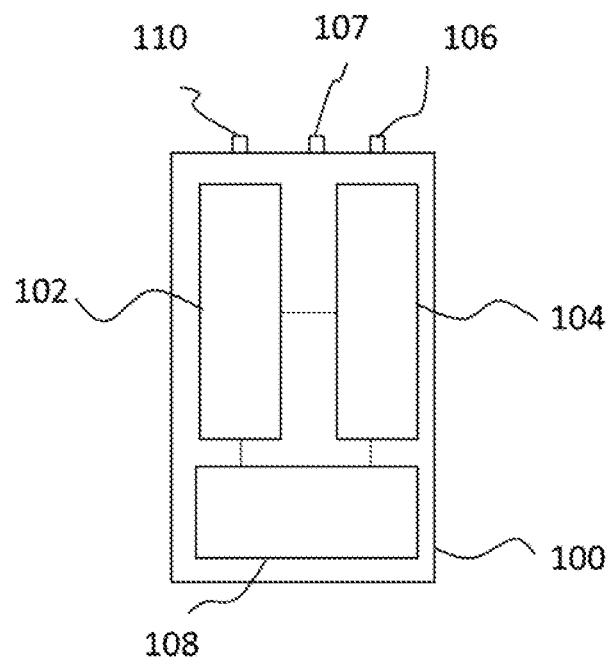
FIG. 1 illustrates a schematic of an exemplary portable electronic device consistent with various disclosed embodiments.

FIG. 1 illustrates a schematic of an exemplary portable electronic device consistent various disclosed embodiments. In FIG. 1, the portable electronic device 100 such as a power bank, a monitor or a lamp, is used as an example to illustrate various embodiments of the present disclosure. In this embodiment, the portable electronic device 100 includes a power management circuit 102, a TENS, circuit 104, a first output unit 106, a second output unit 107, and a battery 108. The power management circuit 102 may be a power management circuit or a power management module in a power bank or a portable charger, or the power management circuit for other devices such, as monitor, MP3, PDA, iPad, tablet, remote, table lamp, and laptop, etc. The TENS circuit 104 may provide stimulating pulses to the user's skin through the first output unit 106. The battery 108 may include nickel-cadmium (NiCd), nickel-zinc (NiZn), nickel metal hydride (NiMH), lithium-ion (Li-ion) battery, or other types of batteries suitable for the portable electronic device. The power bank may provide a power supply to the user through the second output unit 107.

In one embodiment of the present disclosure, the portable electronic device 100 comprises a power bank, the power management circuit 102 of the power bank may manage the power distribution between the power bank and the TENS circuit 104. In this embodiment, the user may use the power bank and the TENS individually or simultaneously through the one or more output units 106 and 107. The first output unit 106 for providing the TENS function may be a 3.5 mm pin connector, 2.5 mm pin connector, 2.35 mm pin connector, 2 mm pin connector, 3.5 mm snap connector, 2.5 mm snap connector, 2.35 mm snap connector, 2 mm snap connector, or other types of connectors applicable to supplying TENS current. The second output unit 107 for providing the power bank function may be a USB connector, mini USB connector, micro USB connector, USB-C connector, or other types of connectors applicable to supplying power energy.

In this embodiment, the power management circuit 102 may monitor the power level of the battery 108. When the power level of the battery 108 is higher than a threshold value, the power management circuit 102 may allow both the power bank function and the TENS function to be turned on individually or simultaneously. When the power level of the battery 108 is equal to or lower than the threshold value, the portable electronic device may enter a power saving mode and the power management circuit 102 may limit or turn off the TENS circuit 104 and allow only the power bank to be turned on.

In another embodiment, the power management circuit 102 may monitor the power level of the battery 108. When the power level of the battery 108 is higher than a threshold value, the power management circuit 102 may allow the TENS circuit 104 to provide a full range of amplitude and frequency of the TENS function. When the power level of the battery 108 is equal to or lower than the threshold value, the portable electronic device may enter a power saving mode and the power management circuit 102 may limit the amplitude or frequency of the TENS function provided by the TENS circuit 104 under a predefined range.

In another embodiment, the power management circuit 102 may monitor the temperature of the battery 108. When the temperature of the battery 108 is higher than a pre-defined value, the power management circuit 102 may limit or automatically turn off the TENS circuit 104. By monitoring the temperature of the battery 108, the overheated hazard of the power bank may be prevented in advance by the power management circuit 102. In another embodiment, When the temperature of the battery 108 is higher than a pre-defined value, the power management circuit 102 may limit the operational amplitude or frequency of the TENS circuit 104 to prevent the overheated hazard of the power bank.

Referring to FIG. 1 again, the portable electronic device 100 may further include a charging connecter 110 for charging the battery 108 by an external power source. The charging connecter 110 may be a USB connector, mini USB connector, micro USB connector, USB-C connector, or other types of connectors applicable to supplying power energy. When the battery 108 of the power bank is charged by an external power source, the power management circuit 102 may switch the power supply path of the TENS circuit 104 from the battery 108 to the external power source. In other words, in this situation where the power bank is under the charging mode, the power management circuit 102 may control the TENS circuit 104 to be powered by the external power source through the charging connecter 110. The external power source provides the power energy to the battery 108 and the TENS circuit 104 as well.

In another embodiment of the present disclosure, the portable electronic device 100 may comprise a monitor, the power management circuit 102 of the monitor may manage the power distribution between the image displaying and the TENS circuit 104. In this embodiment, the user may use the monitor and the TENS individually or simultaneously through the one or more output units 106 and 107. The first output unit 106 for providing the TENS function may be a 3.5 mm pin connector, 2.5 mm pin connector, 2.35 mm pin connector, 2 mm pin connector, 3.5 mm snap connector, 2.5 mm snap connector, 2.35 mm snap connector, 2 mm snap connector, or other types of connectors applicable to supplying TENS current. The second output unit 107 for providing the image display may be a digital visual interface (DVI), mini-DVI, micro-DVI, high-definition multimedia interface (HDMI), DisplayPort, Thunderbolt, USB-C connector, or other types of connectors applicable to transmitting image data.

In another embodiment of the present disclosure, the portable electronic device 100 may comprise a lamp, the power management circuit 102 of the lamp may manage the power distribution between the lamp power supply and the TENS circuit 104. In this embodiment, the user may use the lamp and the TENS individually or simultaneously through the one or more output units 106 and 107. The first output unit 106 for providing the TENS function may be a 3.5 mm pin connector, 2.5 mm pin connector, 2.35 mm pin connector, 2 mm pin connector, 3.5 mm snap connector, 2.5 mm snap connector, 2.35 mm snap connector, 2 mm snap connector, or other types of connectors applicable to supplying TENS current. The second output unit 107 for providing a power supply to drive a lamp may comprise various types of connectors applicable to supplying power energy to drive an internal or external lamp.

As mentioned above, the portable device 100 may be electrical devices such as monitor, MP3, PDA iPad, tablet, remote, table lamp, or laptop, etc., as long as the portable device 100 comprises an additional function that provides the TENS current to a user individually or simultaneously other than a function of monitor, MP3, PDA, iPad, tablet, remote, table lamp, or laptop, etc.

In another embodiment, the portable device 100 may further comprise a biometric detection device for detecting the user's heartbeat, blood pressure, body temperature, or other biometric information. The biometric detection device may be attached to the user's skin or specific portion of the body and communicate with the portable device 100 through a wired or a wireless way. By receiving the biometric information from the biometric detection device, the power management circuit 102 may distribute the power accordingly. For example, when the heartbeat of the user is detected increased, the user may factually feel uncomfortable. The power management circuit 102 may reduce the power of the TENS output. For another example, when the heartbeat of the user exceeds a predefined value, the power management circuit 102 may turn off the TENS output. For another example, when the heartbeat of the user exceeds a predefined value, the device may give advice to apply the electrode to some particular locations of the body that can relieve the heartbeat or blood increase. For another example, the biometric detection device may connect and communicate with the portable electronic device 100 through Infrared radiation (IR) WiFi, Bluetooth communication, or other wireless communications.

In a further embodiment, the biometric detection device may connect and communicate with the portable electronic device 100 locally or remotely from a server end through the Internet. For example, the biometric detection device may collect the user's heartbeat, blood pressure, body temperature, or other biometric information, and upload these information to a server through the Internet. When the portable electronic device 100 is turned on, the portable electronic device 100 may obtain the user's heartbeat, blood pressure, body temperature, or other biometric information from the server through the Internet, and then adjust the power management of the TENS function accordingly or provide suggestions to stimulation some particular locations to relieve the symptom.

Figure 2:
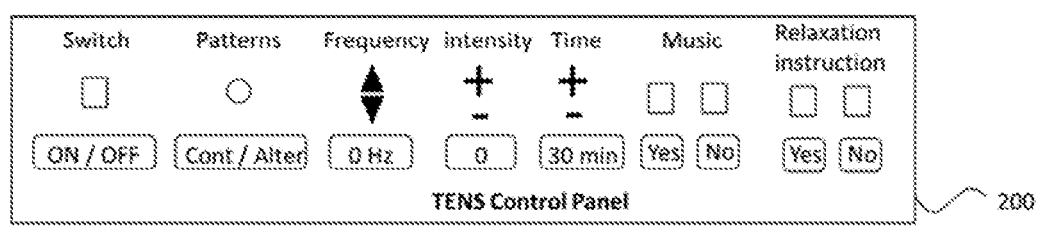
FIG. 2 illustrates a schematic of an exemplary TENS control panel of a portable electronic device consistent with various disclosed embodiments.

Further, the portable electronic device 100 may include a control, panel for a user to control the functions of the TENS, as shown in FIG. 2 FIG. 2 illustrates a schematic of an exemplary TENS control panel of a portable electronic device consistent with various disclosed embodiments. The TENS control panel 200 includes various buttons for controlling various functions of the TENS. For example, the TENS control panel 200 may include a pattern control button to control the operational modes of the TENS to work continuously or alternatively. For another example, the TENS control panel 200 may include a frequency control button to adjust the frequency of the TENS electrical current. By adjusting the frequency of the TENS electrical current, a stimulation function and a massage function may be provided to the user in the same portable electronic device. For a further example, the TENS control panel 200 include an intensity control button to control the intensity of the TENS.

The appearance and the functions of the control panel 200 may be designed based on various requirements. For example, the control panel 200 may further include a switch button for turning on/off the portable electronic device 100, a timer button to control the power management circuit 102 to turn off or turn on after a certain time, a music button for turning on/off the music while using the TENS function, or an instruction button for turning on/off the relaxation instruction while using the TENS function to enhance the treatment effect of TENS. Furthermore, the timer function may be combined with other functions of the portable electronic device 100, such as frequency adjustment or intensity adjustment, to switch to different operational modes after a certain time. The timing and switching program of the operational modes may be pre-stored in the power management circuit 102 by the device manufacture and may be also programed by the user.

In another embodiment, the control panel 200 may connected to the portable electronic device 100 through a wired or a wireless way. For example, the control panel 200 may designed and embedded on the portable electronic device 100 for control the TENS functions. For another example, the control panel 200 may connect and communicate with the portable electronic device 100 through Infrared radiation (IR), WiFi, Bluetooth communication, or other wireless communications.

Figure 3:
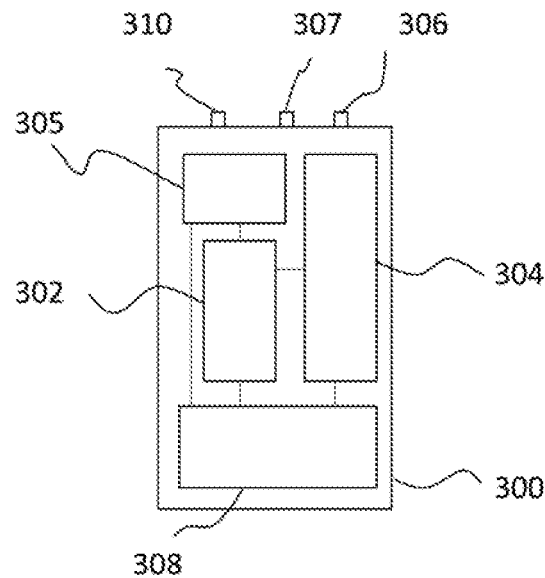
FIG. 3 illustrates a schematic of another exemplary portable electronic device consistent with various disclosed embodiments.

FIG. 3 illustrates a schematic of another exemplary portable electronic device consistent with various disclosed embodiments. In FIG. 3, the portable electronic device 300, such as a cell phone, is used as an example to explain the embodiments of the present disclosure. In this embodiment, the portable electronic device 300 includes a power management circuit 302, a TENS circuit 304, a cellphone circuit 305, a TENS output connector 306, an audio output connector 307, a charging connector 310, and a battery 308.

The power management circuit 302 may be a power management circuit or a power management module in the cell phone. The power management circuit 302 may be connected between the battery 308 and the TENS circuit 304 and the cellphone circuit 305 to control the power distribution between the TENS circuit 304 and the cellphone circuit 305. The TENS circuit 304 may provide stimulating pulses to the user's skin through the first output unit 306. The cellphone circuit 305 may provide all essential functions of a cell phone, such as communication function, information displaying function, data inputting/outputting function, or audio/video outputting function. The battery 308 may include nickel-cadmium (NiCd), nickel-zinc (NiZn), nickel metal hydride (NiMH), lithium-ion (Li-ion) battery, or other types of batteries suitable for the portable electronic device. In some embodiments, the cellphone circuit 305 may provide an audio output to the user through the second output unit 307. The first output unit 306 for providing the TENS function may be a 3.5 mm pin connector, 2.5 mm pin connector, 2.35 mm pin connector, 2 mm pin connector, 3.5 mm snap connector, 2.5 mm snap connector, 2.35 mm snap connector, 2 mm snap connector, or other types of connectors applicable to supplying TENS current. The second output unit 307 for providing the audio output to the user may be a 3.5 mm pin connector, 2.5 mm pin connector, 2.35 mm pin connector, 2 mm pin connector, a USB connector, mini USB connector, micro USB connector, USB-C connector, or other types of connectors applicable to supplying audio signal.

In this embodiment, the power management circuit 302 may monitor the power level of the battery 308. When the power level of the battery 308 is higher than a threshold value, the power management circuit 302 may allow both the cellphone function and the TENS function to be turned on individually or simultaneously. When the power level of the battery 308 is equal to or lower than the threshold value, the portable electronic device may enter a power saving mode and the power management circuit 302 may limit or turn off the TENS circuit 304 and allow only the cellphone function to be turned on.

In another embodiment, the power management circuit 302 may monitor the power level of the battery 308. When the power level of the battery 308 is higher than a threshold value, the power management circuit 302 may allow the TENS circuit 304 to provide a full range of amplitude and frequency of the TENS function. When the power level of the battery 308 is equal to or lower than the threshold value, the portable electronic device may enter a power saving mode and the power management circuit 302 may limit the amplitude or frequency of the TENS function provided by the TENS circuit 304 under a predefined range.

In another embodiment, the power management circuit 302 may monitor the temperature of the battery 308. When the temperature of the battery 308 is higher than a predefined value, the power management circuit 302 may limit or automatically turn off the TENS circuit 304. By monitoring the temperature of the battery 308, the overheated hazard of the power bank may be prevented in advance by the power management circuit 302. In another embodiment, When the temperature of the battery 308 is higher than a pre-defined value, the power management circuit 302 may limit the operational amplitude or frequency of the TENS circuit 304 to prevent the overheated hazard of the cellphone.

The portable electronic device 300 may further include a charging connecter 310 for charging the battery 308 by an external power source. The charging connecter 310 may be a USB connector, mini USB connector, micro USB connector, USB-C connector, or other types of connectors applicable to supplying power energy. When the battery 308 of the cellphone is charged by an external power source, the power management circuit 302 may switch the power supply path of the TENS circuit 304 from the battery 308 to the external power source. In other words, in this situation that the cellphone is under the charging mode, the power management circuit 302 may control the TENS circuit 304 to be powered by the external power source through the charging connecter 310. The external power source provides the power energy to the battery 308 and the TENS circuit 304 as well.

In another embodiment, the portable electronic device 300 may be a smart phone, and the portable electronic device 300 may be further installed a control application. In this embodiment, the definition of the threshold value of the power level or the threshold temperature of the battery 308 may be defined and adjusted by the user through the control application installed in the smart phone. The user may define the threshold value to enter the power saving mode. Further, the user may define turning off the cellphone function and keeping the TENS function on in the power saving mode as desired.

The control application may also display a control panel for a user to control the functions of the TENS. Similar to the control panel 200 shown in FIG. 2 the control application may include various buttons for controlling various functions of the TENS. For example, the control application may include a pattern control button to control the operational modes of the TENS to work continuously or alternatively. For another example, the control application may include a frequency control button to adjust the frequency of the TENS electrical current. By adjusting the frequency of the TENS electrical current, a stimulation function and a massage function may be provided to the user in the same portable electronic device. For a further example the control application may include an intensity control button to control the intensity of the TENS.

The user interface and the functions of the control application may be designed based on various requirements. For example, the control application may further include a timer button to control the power management circuit 302 to turn off or turn on after a certain time. Furthermore, the timer function may be combined with other functions of the portable electronic device 300, such as frequency adjustment or intensity adjustment, to switch to different operational modes after a certain time. The timing and switching program of the operational modes may be pre-stored in the power management circuit 302 by the device manufacture and may be also programed by the user through the control application.

In some embodiments, the user may further set several threshold values of the power level to output the TENS in different amplitude or frequency ranges through the control application. For example, the user may set several amplitude or frequency ranges corresponding to several threshold values, and when the power level of the battery 308 is in different ranges the portable electronic device 300 may enter different power saving modes and provide the TNES function with different amplitudes or frequencies.

In a further embodiment, the user may set several power saving modes through the control application. For example, under different power saving modes, the portable electronic device 300 may be controlled to enable both the cellphone function and the TENS function, enable the cellphone function and disable the TENS function, enable the cellphone function and limit the TENS' amplitude or frequency, or disable the cellphone function and enable the TENS function.

Figure 4:
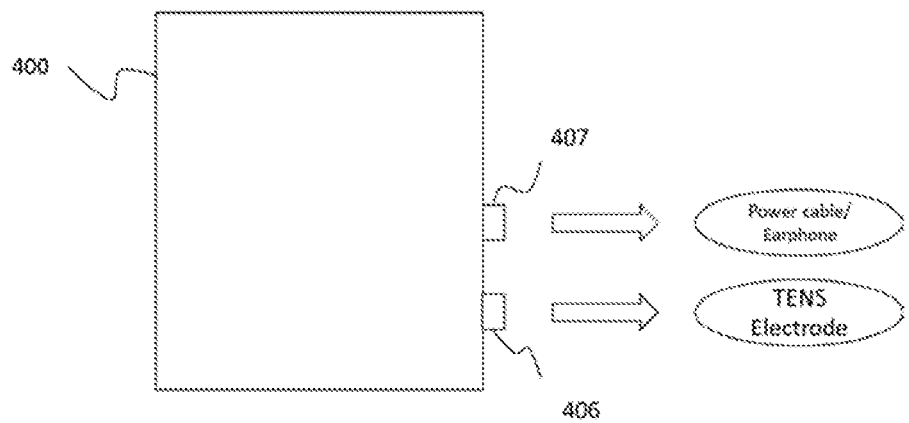
FIG. 4 illustrates a schematic of another exemplary portable electronic device consistent with various disclosed embodiments.

FIG. 4 illustrates a schematic of another exemplary portable electronic device consistent with various disclosed embodiments. In FIG. 4, the first output unit 406 provides the TENS electrical current to a TENS electrode contacting the user's skin, and the second output unit 407 provides the power to another device through the power cable or provides the audio signal to the user through the ear phone separately. The TENS electrical current and the power or audio signal are provided by the battery in the portable electronic device 400.

In some embodiments, the portable electronic device 400 may provide the TENS electrical current and the power or audio signal to the output units 406 and 407 simultaneously. In other embodiments, the portable electronic device 400 may provide the TENS electrical current and the power or audio signal to the output units 406 and 407 alternatively. Because the first output unit 406 and the second output unit 407 are arranged separately in the portable electronic device 400, the first output unit 406 and the second output unit 407 may be operated simultaneously or separately as the user's desire.

In the situation that the portable electronic device 400 provides the TENS electrical current and the power or audio signal to the output unit simultaneously, the first output unit 406 may provide the TENS electrical current to the user through the TENS electrode and the second output unit 407 may provide the power or the audio signal to the user through the power cable or the earphone simultaneously. In other words, the portable electronic device 400 may provide the TENS electrical current and the power or audio signal to the user at the same time.

In the situation that the portable electronic device 400 provides the TENS electrical current and the power or audio signal to the output units 406 and 407 alternatively, the first output unit 406 may provide the TENS electrical current to the user through the TENS electrode and stop providing power or signals to the second output unit 407. After using the TENS function, the portable electronic device 400 may turn off the TENS function to stop providing the TENS electrical current to the first output unit 406, and then enable the power supply or audio signal function of the second output unit 407. In other words, in this embodiment, the portable electronic device 400 may be limited to use only one function at the same time. The purpose of this limitation is to prevent the battery overdrawn when using multiple functions at the same time, and this limitation may be enabled or disabled by the user.

Figure 5:
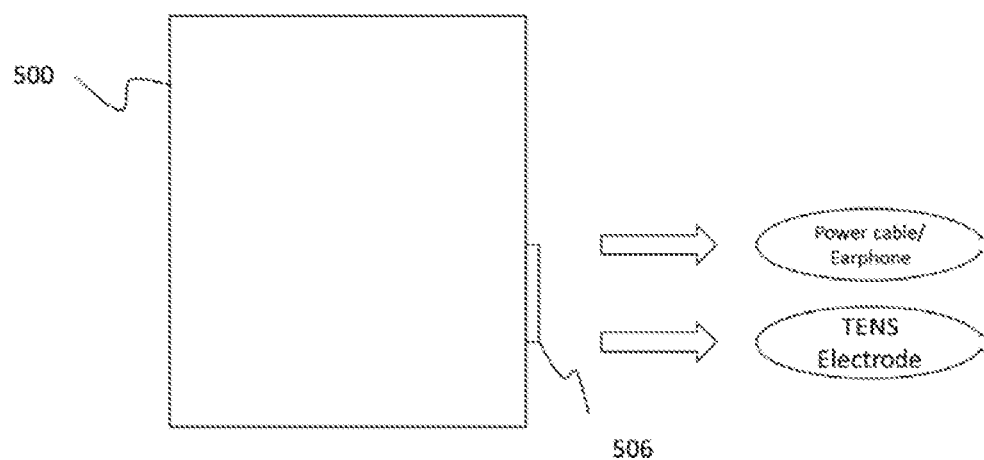
FIG. 5 illustrates a schematic of another exemplary portable electronic device consistent with various disclosed embodiments.

FIG. 5 illustrates a schematic of another exemplary portable electronic device consistent with various disclosed embodiments. In FIG. 5, the portable electronic device 500 includes an integrated output unit 506. The integrated output unit 506 may provide both the TENS electrical current and the power or audio signal to the user. In some embodiments, the TENS stimuli may be applied to the user through a designated TENS output connector, or through a special combo connector that is used as a power supply connector, an audio/video output connector or a TENS output connector. In the situation that the integrated output unit 506 is an integrated connector, the integrated output unit 506 may provide the TENS electrical current, the power supply, or the audio signal to the user or other device through the same integrated connector. The integrated output unit 506 may include a 3.5 mm pin connector, 2.5 mm pin connector, 2.35 mm pin connector, 2 mm pin connector, 3.5 mm snap connector, 2.5 mm snap connector, 2.35 mm snap connector, 2 mm snap connector, a USB connector, mini USB connector, micro USB connector, USB-C connector, or other types of connectors applicable to provide an integrated function.

In some embodiments, the TENS stimuli may be applied through the designated TENS superficial electrodes designed for contacting different locations of the user's body, including the user's ears. The designated TENS superficial electrodes may be provided in the format of pads, wraps, probes or needles. TENS stimuli output may also be combined with other wearable device such as earphone/headphone.

Figure 6:
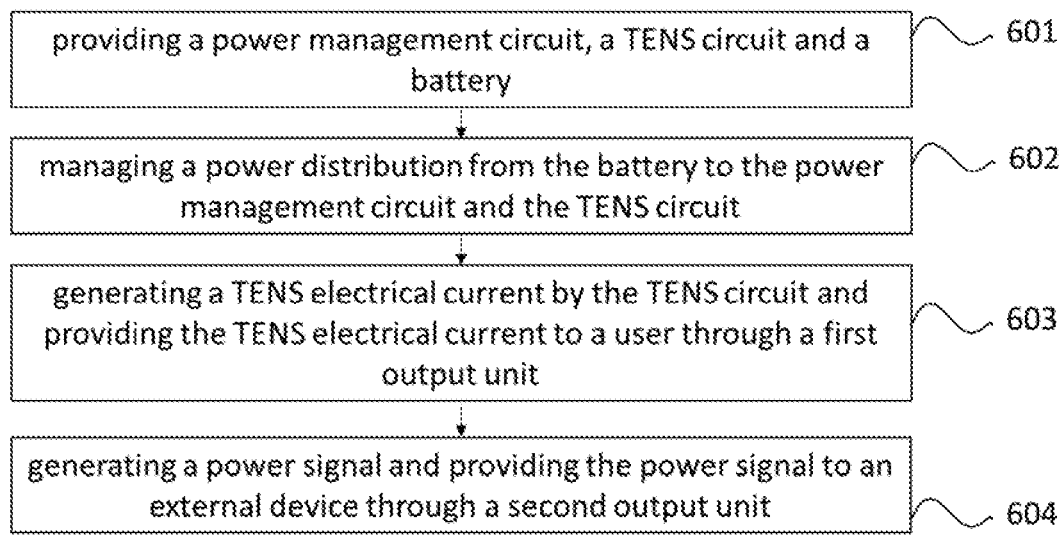
FIG. 6 illustrates a flow chart of an exemplary method for providing a TENS function and a power supply function in a portable electronic device consistent with various disclosed embodiments.

FIG. 6 illustrates a flow chart of an exemplary method for providing a TENS function and a power supply function in a portable electronic device consistent with various disclosed embodiments.

In step 601, a power management circuit, a TENS circuit and a battery are provided. The power management circuit may be a power management circuit or a power management module in a power bank or a portable charger, or the power management circuit for other devices such as monitor, MP3, PDA, iPad, tablet, remote, table lamp, and laptop, etc. The TENS circuit may provide stimulating pulses to the user's skin through the first output unit. The battery may include nickel-cadmium (NiCd), nickel-zinc (NiZn), nickel metal hydride (NiMH) lithium-ion (Li-ion) battery, or other types of batteries suitable for the portable electronic device.

In step 602, the power management circuit further manages the power distribution from the battery to the TENS circuit. In one embodiment of the present disclosure, the portable electronic device comprises a power bank, the power management circuit of the power bank may manage the power distribution between the power bank and the TENS circuit. Furthermore, the user may use the power bank and the TENS individually or simultaneously through the one or more output units.

In step 603, the TENS circuit generates a TENS electrical current end provides the TENS electrical current to a user through a first output unit. The first output unit for providing the TENS function may be a 3.5 mm pin connector, 2.5 mm pin connector, 2.35 mm pin connector, 2 mm pin connector, 3.5 mm snap connector, 2.5 mm snap connector, 2.35 mm snap connector, 2 mm snap connector, or other types of connectors applicable to supplying TENS current.

In step 604, the battery provides the power signal to an external device through a second output unit. The second output unit for providing the power bank function may be a USB connector, mini USB connector, micro USB connector, USB-C connector, or other types of connectors applicable to supplying power energy.

In some embodiments, the power management circuit may further monitor the power level of the battery. When the power level of the battery is higher than a threshold value, the power management circuit may allow both the power bank function and the TENS function to be turned on individually or simultaneously. When the power level of the battery is equal to or lower than the threshold value, the portable electronic device may enter a power saving mode and the power management circuit may limit or turn off the TENS circuit and allow only the power bank to be turned on.

In some embodiments, the power management circuit may further monitor the power level of the battery. When the power level of the battery is higher than a threshold value, the power management circuit may allow the TENS circuit to provide a full range of amplitude and frequency of the TENS function. When the power level of the battery is equal to or lower than the threshold value, the portable electronic device may enter a power saving mode and the power management circuit may limit the amplitude or frequency of the TENS function provided by the TENS circuit under a predefined range.

In another embodiment, the power management circuit may monitor the temperature of the battery. When the temperature of the battery is higher than a pre-defined value, the power management circuit may limit or automatically turn off the TENS circuit. By monitoring the temperature of the battery, the overheated hazard of the power bank may be prevented in advance by the power management circuit. In another embodiment, When the temperature of the battery is higher than a pre-defined value, the power management circuit may limit the operational amplitude or frequency of the TENS circuit to prevent the overheated hazard of the power bank.

The apparatus and methods disclosed herein is to incorporate health prevention and therapeutic function to power bank, cell phone and other consumer electronic devices as mentioned above. When combined with other APPs such as reminding the consumer to apply treatment or stimulation, the embodiments of the present disclosure may significantly enhance the compliance of the treatment. The device may comprise an assembly that providing multiple types of stimuli, which may be used as stimulation and massage while the user enjoys the usual usage of their cell phone.

Other embodiments of the disclosure will be apparent to those skilled in the art from consideration of the specification and practice of the invention disclosed herein. It is intended that the specification and examples be considered as exemplary only, with a true scope and spirit of the invention being indicated by the claims.

What is claimed is:
1. A portable electronic device comprising:
a battery;

a transcutaneous electrical nerve stimulation (TENS) circuit for providing a TENS electrical current;
a cellphone circuit for providing at least a communication function and an audio outputting function;
a power management circuit configured to monitor a power level of the battery, wherein the power management circuit is coupled to the TENS circuit, the cellphone circuit and the battery for managing a power distribution between the TENS circuit and the cellphone circuit;
a first output unit receiving the TENS electrical current from the TENS circuit and outputting the TENS electrical current to a user; and
a second output unit receiving an audio signal from the cellphone circuit and outputting the audio signal to the user, wherein:
when the power level is higher than a threshold value, the power management circuit enables the TENS electrical current to be provided to the first output unit and a power signal to be provided to the second output unit; and
when the power level is lower than or equal to the threshold value, the power management circuit turns off the TENS circuit or limits an output amplitude or an output frequency of the TENS circuit.

2. The portable electronic device according to claim 1, wherein the TENS circuit provides the TENS electrical current to the first output unit and the cellphone circuit provides the audio signal to the second output unit simultaneously.

3. The portable electronic device according to claim 1, wherein the TENS circuit provides the TENS electrical current to the first output unit and the cellphone circuit provides the audio signal to the second output unit alternatively.

4. The portable electronic device according to claim 1, wherein the power management circuit further monitors a temperature of the battery;
when the temperature of the battery is lower than a pre-defined value, the power management circuit enables the TENS electrical current and a power signal to be outputted; and
when the temperature of the battery is higher than or equal to the pre-defined value, the power management circuit turns off the TENS circuit or limits an output amplitude or an output frequency of the TENS circuit.

5. The portable electronic device according to claim 1, wherein the portable electronic device is installed a control application program for setting up the power management circuit.

6. The portable electronic device according to claim 5, wherein the control application comprises a control panel having a plurality of control buttons to control at least one function of the TENS circuit, wherein the plurality of control buttons comprises at least one of a power switch button, a pattern control button, a frequency control button, an intensity control button, a timer setting button, a music switch button, and an instruction switch button.

7. A portable electronic device comprising:
a battery;
a transcutaneous electrical nerve stimulation (TENS) circuit for providing a TENS electrical current;
a first output unit receiving the TENS electrical current from the TENS circuit and outputting a first signal to a user, wherein the first signal comprises the TENS electrical current;
a second output unit outputting a second signal to an external electronic device, the second signal being an audio signal; and
a power management circuit configured to monitor a power level of the battery, wherein the power management circuit is coupled to the battery and the TENS circuit for managing a power distribution between the first signal and the second signal, wherein:
when the power level is higher than a threshold value, the power management circuit enables the TENS electrical current to be provided to the first output unit and a power signal to be provided to the second output unit;
when the power level is lower than or equal to the threshold value, the power management circuit turns off the TENS circuit or limits an output amplitude or an output frequency of the TENS circuit; and
the electronic device includes one of a portable charger, a power bank, an MP3 player, a personal digital assistant (PDA), an iPad, a tablet, a remote-control, a laptop, a desktop, a radio and a monitor.

8. The portable electronic device according to claim 7, wherein when the second signal is a power signal, the power management circuit manages the power distribution between the TENS circuit and the power signal.

9. The portable electronic device according to claim 8, wherein the TENS electrical current is provided to the first output unit and the power signal is provided to the second output unit simultaneously.

10. The portable electronic device according to claim 8, wherein the TENS electrical current is provided to the first output unit and the power signal is provided to the second output unit alternatively.

11. The portable electronic device according to claim 8, wherein:
the power management circuit further monitors a temperature of the battery;
when the temperature of the battery is lower than a pre-defined value, the power management circuit enables the TENS electrical current and a power signal to be outputted; and
when the temperature of the battery is higher than or equal to the pre-defined value, the power management circuit turns off the TENS circuit or limits an output amplitude or an output frequency of the TENS circuit.

12. The portable electronic device according to claim 8, further comprising:
a control panel having a plurality of control buttons to control at least one function of the TENS circuit, wherein the plurality of control buttons comprises at least one of a power switch button, a pattern control button, a frequency control button, an intensity control button, a timer setting button, a music switch button, and an instruction switch button.

13. The portable electronic device according to claim 7, further comprising:
a biometric detection device for detecting at least one of a heartbeat information, a blood pressure information and a body temperature information of the user; wherein the biometric detection device is attached to the user and communicates with the portable device through a wired connection or a wireless connection.

14. The portable electronic device according to claim 13, wherein the biometric detection device transmits the at least one of the heartbeat information, the blood pressure information and the body temperature information of the user to a server, and the power management circuit manages the power distribution between the first signal and the second signal based on a control signal from the server.

15. The portable electronic device according to claim 14, wherein the power management circuit receives the control signal locally or remotely through Internet to adjust the TENS electrical current.

16. A method for providing a transcutaneous electrical nerve stimulation (TENS) function in a portable electronic device, comprising:
provlding a power management circuit, a TENS circuit and a battery, wherein the power management circuit is configured to monitor a power level of the battery;
managing a power distribution from the battery to the power management circuit and the TENS circuit;
generating a TENS electrical current by the TENS circuit and in response to the power level of the battery being higher than a threshold value, providing the TENS electrical current to a user through a first output unit, and in response to the power level of the battery being lower than or equal to the threshold value, turning off the TENS circuit or limiting an output amplitude or an output frequency of the TENS circuit; and
generating a power signal and in response to the power level of the battery being higher than the threshold value, providing the power signal to an external device through a second output unit.

17. The method according to claim 16, further comprising:
monitors a temperature of the battery;
when the temperature of the battery is lower than a pre-defined value, enabling the TENS electrical current and the power signal to be outputted; and
when the temperature of the battery is higher than or equal to the pre-defined value, turning off the TENS circuit or limiting the output amplitude or the output frequency of the TENS circuit.

* * * * *